United States Patent
Qian et al.

(10) Patent No.: US 11,657,247 B2
(45) Date of Patent: May 23, 2023

(54) ADHESIVE FIDUCIAL MARKERS FOR MEDICAL AUGMENTED REALITY

(71) Applicant: Medivis, Inc., New York, NY (US)

(72) Inventors: Long Qian, Brooklyn, NY (US); Christopher Morley, New York, NY (US); Osamah Choudhry, New York, NY (US)

(73) Assignee: Medivis, Inc., New York, NY (US)

( * ) Notice: Subject to any disclaimer, the term of this patent is extended or adjusted under 35 U.S.C. 154(b) by 0 days.

(21) Appl. No.: 17/709,397

(22) Filed: Mar. 30, 2022

(65) Prior Publication Data
US 2023/0037393 A1 Feb. 9, 2023

Related U.S. Application Data

(63) Continuation-in-part of application No. 17/395,233, filed on Aug. 5, 2021.

(51) Int. Cl.
*A61B 34/20* (2016.01)
*G06K 19/06* (2006.01)

(52) U.S. Cl.
CPC .............................. *G06K 19/06037* (2013.01)

(58) Field of Classification Search
None
See application file for complete search history.

(56) References Cited

U.S. PATENT DOCUMENTS

| | | |
|---|---|---|
| 2008/0228064 A1 | 9/2008 | Krueger et al. |
| 2010/0002921 A1 | 1/2010 | Fenchel et al. |
| 2014/0049629 A1* | 2/2014 | Siewerdsen ............ A61B 34/20 348/77 |
| 2014/0276959 A1* | 9/2014 | Oostman ................... A61F 2/10 606/133 |
| 2015/0265367 A1* | 9/2015 | Gruhler ............ A61B 17/00234 600/424 |
| 2018/0193097 A1 | 7/2018 | Mclachlin et al. |
| 2018/0253856 A1 | 9/2018 | Price et al. |
| 2020/0005486 A1 | 1/2020 | Sinha et al. |
| 2020/0352655 A1 | 11/2020 | Freese |
| 2021/0378756 A1* | 12/2021 | Calloway ............... A61B 34/20 |

* cited by examiner

*Primary Examiner* — Patricia J Park
(74) *Attorney, Agent, or Firm* — Cognition IP, P.C.; Edward Steakley; Rajesh Fotedar

(57) ABSTRACT

Various embodiments of a physical instrument are described herein. The physical instrument comprises a reference array platform having a top surface and a bottom surface. A reference array including one or more different fiducial markers is disposed on the top surface of the reference array platform. The reference array platform may have a bent physical configuration or a tilted physical configuration. An adhesive layer is disposed on the bottom surface of the reference array platform.

12 Claims, 3 Drawing Sheets

ADHESIVE FIDUCIAL MARKERS FOR MEDICAL AUGMENTED REALITY

CROSS REFERENCE TO RELATED APPLICATION

This application is a Continuation-in-Part, and claims the benefit of, U.S. patent application Ser. No. 17/395,233 filed on Aug. 5, 2021, which is incorporated herein by reference in its entirety.

BACKGROUND

Current conventional systems have limitations with regard to two-dimensional (2D) and three-dimensional (3D) images in surgical settings. Surgical planning and surgical navigation are necessary for every surgery (or any type of medical procedure). A surgeon and their team must have a plan for a case before entering an operating room, not just as a matter of good practice but to minimize malpractice liabilities and to enhance patient outcomes. Surgical planning is often conducted based on medical images including DICOM scans (MRI, CT, etc.), requiring the surgeon to flip through numerous views/slices, and utilizing this information to imagine a 3D model of the patient so that the procedure may be planned. Accordingly, in such a scenario, the best course of action is often a surgeon's judgment call based on the data that they are provided.

SUMMARY

Conventional systems are deficient with respect to tracking fiducial markers disposed on physical instruments and on patients. Often, such conventional systems are limited in their ability to generate, render and accurately apply virtual interactions in an augmented reality environment based on physical orientations and positions resulting from movement and manipulation of physical instruments with respect to the orientation and position of a physical landmark identified as a location on a patient's body.

Various embodiments of a reference array platform are described herein. A reference array platform may include a reference array. A reference array may include a plurality of different codes. Each code may be a different fiducial marker. The reference array platform may have an adhesive backing suitable for adhesion to human skin. A reference array may include one or more fiducial markers (or codes) disposed on the reference array platform and composed of a non-reflective material that absorbs light (i.e. visible light).

According to various embodiments, a reference array platform with a reference array may have a bent physical configuration. According to various embodiments, a reference array platform with a reference array may have a tilted physical configuration.

According to various embodiments, a reference array platform with a reference array may have one or more insertion areas. For example, an insertion area may be part of a bottom surface of the reference array platform. The bottom surface of the reference array platform may have an adhesive layer for adhesion to an individual.

It is understood that the various embodiments of the reference array platform may be utilized in conjunction with an augmented reality (AR) display system. For example, the AR display system may be one or more embodiments of a Registration Engine as described in U.S. patent application Ser. No. 17/148,522 filed on Jan. 13, 2021, which is incorporated herein by reference in its entirety.

One or more embodiments of a reference array platform described herein may be utilized for placement on—and adhesion to—various locations of a patient's body to indicate a respective position and orientation of a physical landmark on the patient's body. For example, a physical landmark may be location of a physical region of the patient's anatomy. The Registration Engine may generate an AR display of various types of medical data at an AR headset device in alignment with the physical anatomical region(s) of the patient at which respective reference array platforms have been placed.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein.

DETAILED DESCRIPTION

Figure 1:
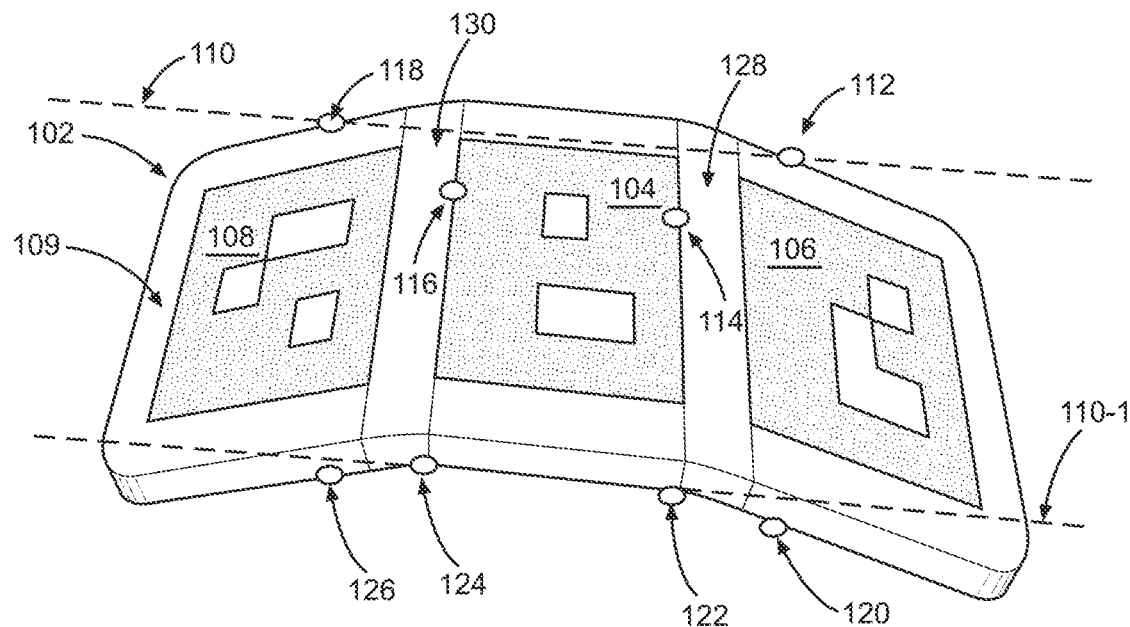
FIG. 1 is a diagram illustrating a type of perspective view of an exemplary embodiment.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

As shown in FIG. 1, the reference array platform 102 may have a bent physical configuration. The reference array platform 102 may include a reference array disposed on the top surface of the reference array platform 102. In some embodiments, the reference array may include one or more codes 104, 106, 108. In some embodiments, the codes 104, 106, 108 may be different hamming codes. In some embodiments, the reference array platform may include one or more fiducial markers.

The one or more codes 104, 106, 108 may be composed of a non-reflective material that absorbs light. As such, various embodiments of the reference array platform may be tracked by a visible light camera, thereby alleviating the requirement of utilizing an infrared tracking system typically found in conventional systems. In some embodiments, the reference array platform 102 may be composed of a plastic nylon material, stainless steel or aluminum. In some embodiments, the reference array platform 102 may have a composition that includes a sterilized material, such as a material sterilized via gamma-sterilization or auto-clave.

A padding 109 may further be disposed on the reference array platform 102. For example, the padding 109 may border one or more edges of each of the codes 104, 106, 108 on the reference array platform 102. The area on the top surface that includes a code 108 and its padding 109 may be a particular code region of the reference array platform 102.

An intermediary panel 128 may be situated between a first code region of a first code 104 and a second code region of a second code 106. Another intermediary panel 130 may be situated between the first code region of the first code 104 and a third code region of a third code 108. In some embodiments, a portion of an edge of an intermediary panel 128, 130 is in contact with an edge of a code 104, 106, 108. In addition, other portions of the edge of the intermediary panel 128, 130 may further be in contact with a portion of padding 109. In some embodiments, any intermediary panel may also be a curved panel.

FIG. 1 further includes illustration of a first reference horizontal line 110 that is in alignment with the position and orientation of the portion of the top surface of the reference array platform 102 that includes the first code 104. Reference locations 112, 114, 116, 118 are further illustrated. Some reference locations 112, 118 refer to a location on the horizontal line 110 and some reference locations 114, 116 refer to a location at the first code 104. An angle between a reference location 112 and reference location 114 may be one of 10, 15 and 20 degrees. As such, the reference array platform 102 has a bent physical configuration due to the intermediary panel 128, the second code 106 and the code region of the second code 106 being oriented at a downward angle from the first code 104 and the code region of the first code 104 according to one of 10, 15 and 20 degrees.

An angle between a reference location 118 and reference location 116 may be one of 10, 15 and 20 degrees. As such, the reference array platform 102 has a bent physical configuration due to the intermediary panel 130, the third code 108 and the code region of the third code 108 being oriented at a downward angle from the first code 104 and the code region of the first code 104 according to one of 10, 15 and 20 degrees.

FIG. 1 further includes an illustration of a second reference horizontal line 110-1 parallel with the first horizontal line 110. Reference locations 120, 122, 124 126 are further illustrated. Some reference locations 122, 124 refer to a location on the second horizontal line 110-1. A reference location 120 refers to a location at a portion the reference array platform 102 that corresponds with the code region of the second code 106. Another reference location 126 refers to a location at a portion the reference array platform 102 that corresponds with the code region of the third code 108.

An angle between reference locations 120, 122 may be one of 160, 165 and 170 degrees. That is, the bent physical configuration of the reference array platform 102 that includes the intermediary panel 128, the second code 106 and the code region of the second code 106 being oriented at a downward angle of 10, 15 or 20 degrees results in the angle between the reference locations 120, 122 being 170, 165 or 160, respectively.

An angle between reference locations 124, 126 may be one of 160, 165 and 170 degrees. That is, the bent physical configuration of the reference array platform 102 that includes the intermediary panel 130, the third code 108 and the code region of the third code 108 being oriented at a downward angle of 10, 15 or 20 degrees results in the angle between the reference locations 124, 126 being 170, 165 or 160, respectively. It is understood that various embodiments of the reference array platform 102 are not limited solely to angles of 10, 15, 20, 160, 165 and/or 170 degrees.

Figure 2:
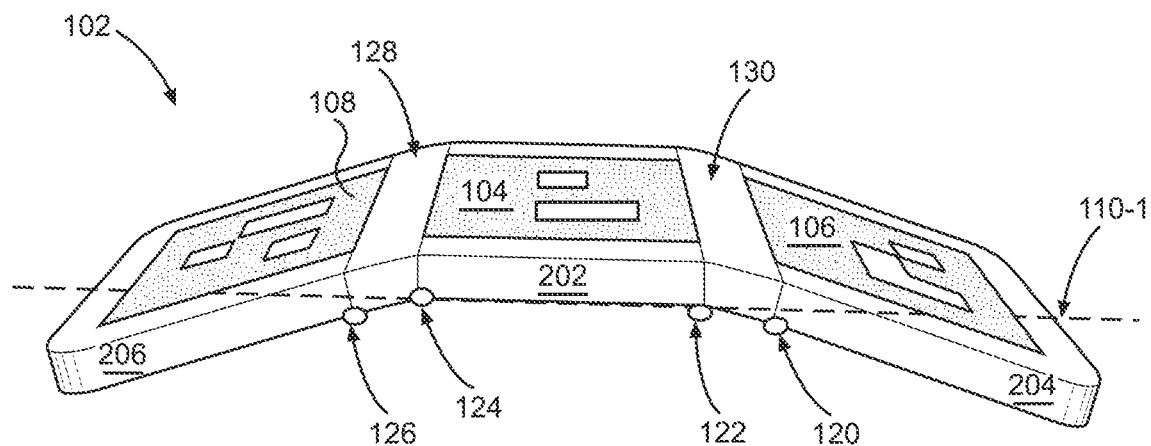
FIG. 2 is a diagram illustrating a type of perspective view of an exemplary embodiment.

As shown in FIG. 2, the reference array platform 102 may have a bent physical configuration and further include a first side portion 202 that corresponds with the code region of the first code 104, a second side portion 204 that corresponds with the code region of the second code 106 and a third side portion 206 that corresponds with the code region of the third code 108. FIG. 2 further provides a different perspective view of the second horizontal line 110-1 and the reference locations 120, 122, 124, 126 of FIG. 1. According to the perspective view, the second horizontal line 110-1 is situated at a position and orientation such that it runs along an edge shared between the first side portion 202 and a bottom surface of the reference array platform 102.

Figure 3:
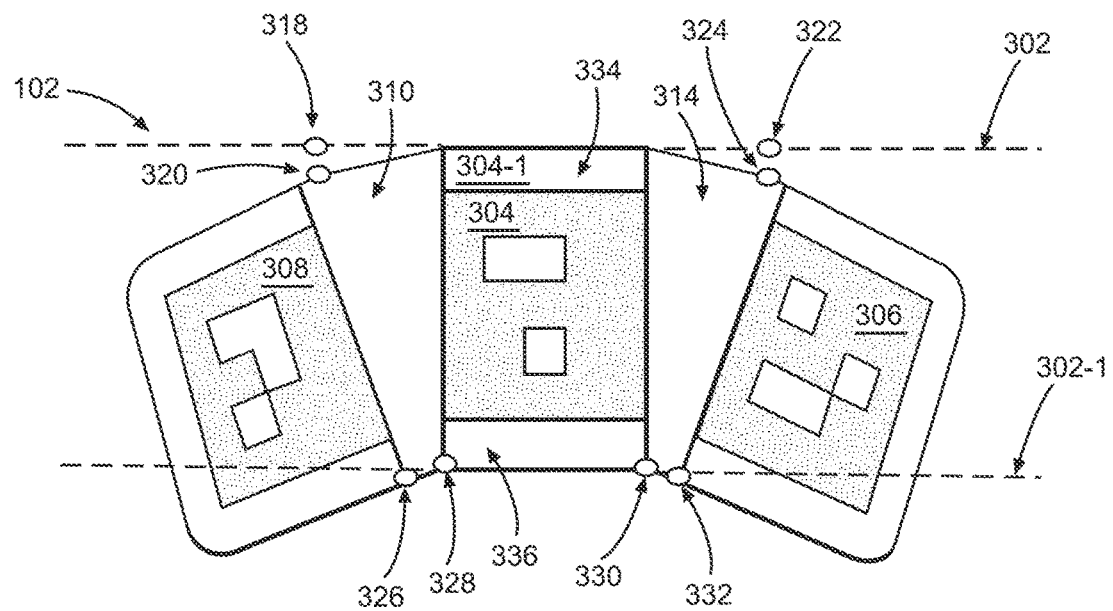
FIG. 3 is a diagram illustrating a type of perspective view of an exemplary embodiment.

According to some embodiments, the reference array platform 102 may have a tilted physical configuration. An overhead view of the reference array platform 102 in the tilted physical configuration is shown in FIG. 3. A first code region 304-1 of a first fiducial marker 304 may be situated between a second code region of a second fiducial marker 306 and a third code region of a third fiducial marker 308. In some embodiments, a code region may consume a square area of the reference array platform 102 of 10 millimeters (mm), 15 mm or 20 mm and have a thickness of: 1 mm, 1.5 mm or 2 mm. A code region may include a fiducial marker and one or more portions of border padding surrounding the fiducial marker. In some embodiments, an edge of the code region may also be an edge of the corresponding fiducial marker while the remaining edges of the code region may include border padding. For example, the first code region 304-1 is defined as having two parallel edges that are each in alignment with edges of the fiducial marker 304. The first code region is further defined as also having other parallel edges in alignment with edges of border padding as well. In some embodiments, border padding may a portion of the reference array platform that does not include any portion of a fiducial marker.

A first intermediary triangular panel 310 may be disposed between the first code region 304-1 and the third code region. A third intermediary triangular panel 314 may be disposed between the first code region 304-1 and the second code region.

FIG. 3 further includes an illustration of a third reference horizontal line 302 and a fourth reference horizontal line 302-1. The third reference horizontal line 302 is situated at a position and orientation such that its runs along an edge shared between a padding 334 of the first code region 304-1 and a side portion of the reference array platform 102 that corresponds with the first code region 304-1. The fourth reference horizontal line 302 is situated at a position and orientation such that its runs along an edge shared between a padding 336 of the first code region 304-1 and another side portion of the reference array platform 102 that corresponds with the first code region 304-1. The third reference horizontal line 302 and the fourth reference horizontal line 302-1 run parallel to each other.

Reference locations 318, 320, 322, 324, 326, 328, 330, 332 are further illustrated in FIG. 3. Some reference locations 318, 322 refer to a location on the third horizontal line 302. A reference location 320 refers to a location on the reference array platform 102 that corresponds with the intermediary triangular panel 310. In some embodiments, the reference location 320 may be situated at a portion of an edge of the reference array platform 102 shared by the intermediary triangular panel 310 and a side portion of the reference array platform 102 that corresponds with the intermediary triangular panel 310. It is understood that various embodiments of the reference array platform 102 may have any number of intermediary panels between respective code regions. It is further understood that various embodiments of the reference array platform 102 may have intermediary panels of various shapes and the reference array platform 102 is not limited solely to intermediary triangular panels. It is also further understood that various embodiments of the reference array platform 102 may have various intermediary panels of differing shapes included in a same instance of the reference array platform 102.

An angle between the reference location 318 and the reference location 320 may be one of 10, 15 and 20 degrees. As such, the top surface of the reference array platform 102, as viewed via an overhead perspective, has a tilted physical configuration due to the intermediary triangular panel 310 and the third code region being oriented at a downward angle from the first code region 304-1 according to one of 10, 15 and 20 degrees.

Another reference location 324 refers to a location on the reference array platform 102 that corresponds with an intermediary triangular panel 314. In some embodiments, the reference location 324 may be situated at a portion of an edge of the reference array platform 102 shared by the intermediary triangular panels 314 and a side portion of the reference array platform 102 that corresponds with the intermediary triangular panel 314.

An angle between the reference location 322 and the reference location 324 may be one of 10, 15 and 20 degrees. As such, the top surface of the reference array platform 102, as viewed via an overhead perspective, has a tilted physical configuration due to the intermediary triangular panel 314 and the third code region being oriented at a downward angle from the first code region 304-1 according to one of 10, 15 and 20 degrees.

Some reference locations 328, 330 refer to a location on the fourth horizontal line 302-1. A reference location 326 refers to a location on the reference array platform 102 that corresponds with the intermediary triangular panel 310. In some embodiments, the reference location 326 may be situated at a portion of an edge of the reference array platform 102 shared by the intermediary triangular panel 310 and a side portion of the reference array platform 102.

An angle between the reference location 326 and the reference location 328 may be one of 170, 165 and 160 degrees. That is, when the tilted physical configuration of the reference array platform 102 includes a downward angle of the intermediary triangular panel 310 and the third code region of 10, 15 or 20 degrees, then the angle between the reference locations 326, 328 will be 170, 165 or 160, respectively.

A reference location 332 refers to a location on the reference array platform 102 that corresponds with an intermediary triangular panel 314. In some embodiments, the reference location 332 may be situated at a portion of an edge of the reference array platform 102 shared by one the intermediary triangular panel 314 and a side portion of the reference array platform 102.

An angle between the reference location 330 and the reference location 332 may be one of 170, 165 and 160 degrees. That is, when the tilted physical configuration of the reference array platform 102 includes a downward angle of the intermediary triangular panel 314 and the second code region 306-1 of 10, 15 or 20 degrees, then the angle between the reference locations 330, 332 will be 170, 165 or 160, respectively.

Figure 4A:
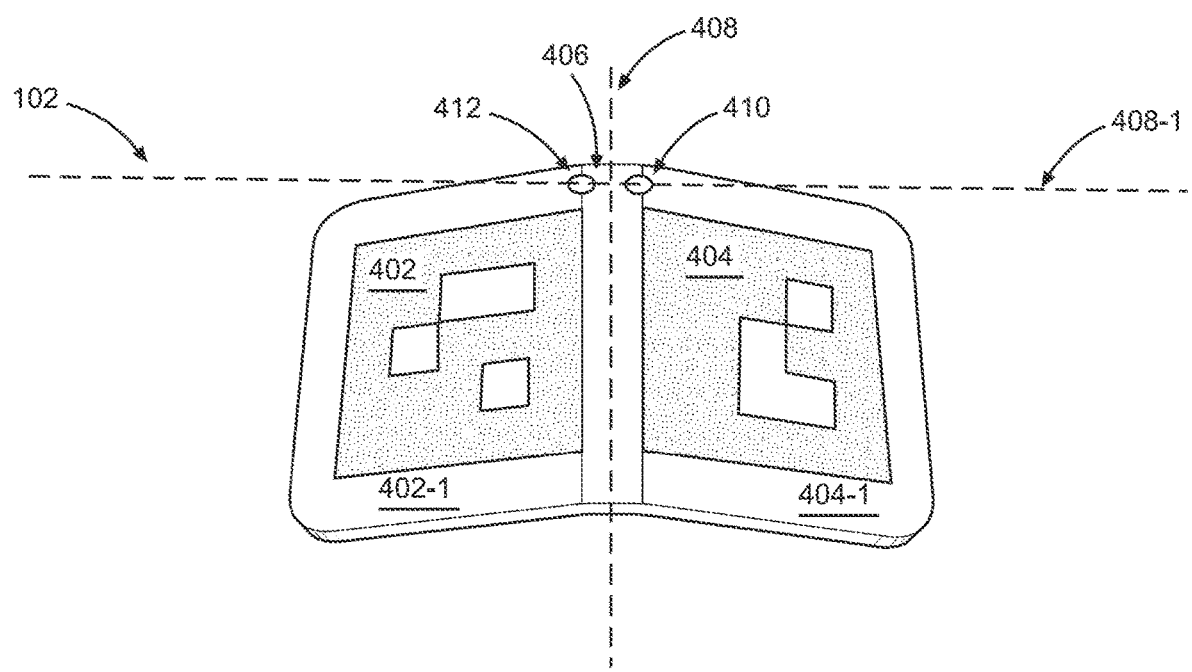
FIGS. 4A-4B are each a diagram illustrating a type of perspective view of an exemplary embodiment.

A perspective view of the reference array platform 102 with a bent physical configuration is shown in FIG. 4A. A reference array may be disposed on the top surface of the reference array platform 102. The reference array may include two different fiducial markers 402, 404 in respective code regions 402-1, 404-1. However, according to various embodiments, a reference array may have any number of codes and/or fiducial markers. In some embodiments, multiple codes and/or fiducial markers may be included within a same code region. In some embodiments, an edge of a code region 402-1, 404-1 may be aligned with an edge of a corresponding fiducial marker 402, 404. The remaining edges of the code region 402-1, 404-1 may include portions of the reference array platform 102 that surround the other sides of the code region 402-1, 404-1.

An intermediary panel 406 may be situated between the code regions 402-1, 404-1. FIG. 4A further includes an illustration of a fifth reference horizontal line 408 situated at a position and orientation such that its runs along the center of the intermediary panel 406. A sixth reference horizontal line 408-1 is presented as well. Reference locations 410, 412 are further illustrated in FIG. 4A. A reference location 412 refers to a location on the reference array platform 102 that corresponds with an edge shared between the intermediary panel 406 and a code region 402-1. A reference location 410 refers to a location on the reference array platform 102 that corresponds with an edge shared between the intermediary panel 406 and a code region 404-1.

Figure 4B:
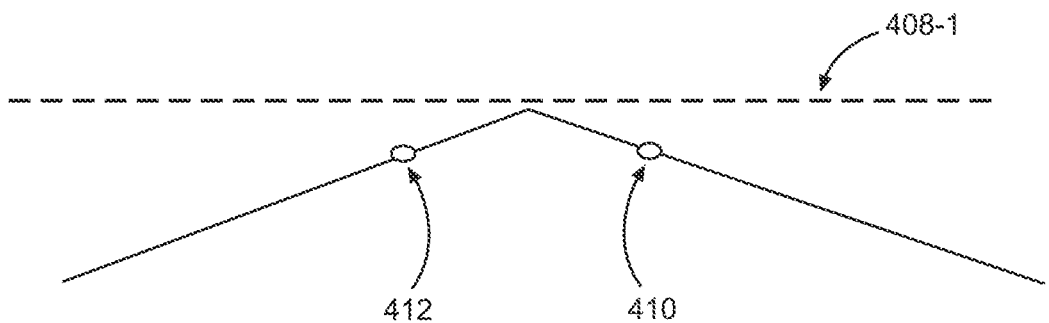

FIG. 4B illustrates a diagram showing a spatial relationship between reference locations 410, 412 and the sixth reference horizontal line 408-1. An angle between the reference location 410 and the horizontal line 408-1 may be 10, 15 or 20 degrees. An angle between the reference location 412 and the horizontal line 408-1 may also be 10, 15 or 20 degrees. It is noted that in various embodiments, the respective angles between the reference locations 410, 412 and the horizontal line 408-1 may be the same. In various embodiments, the respective angles between the reference locations 410, 412 and the horizontal line 408-1 may be different.

Figure 5:
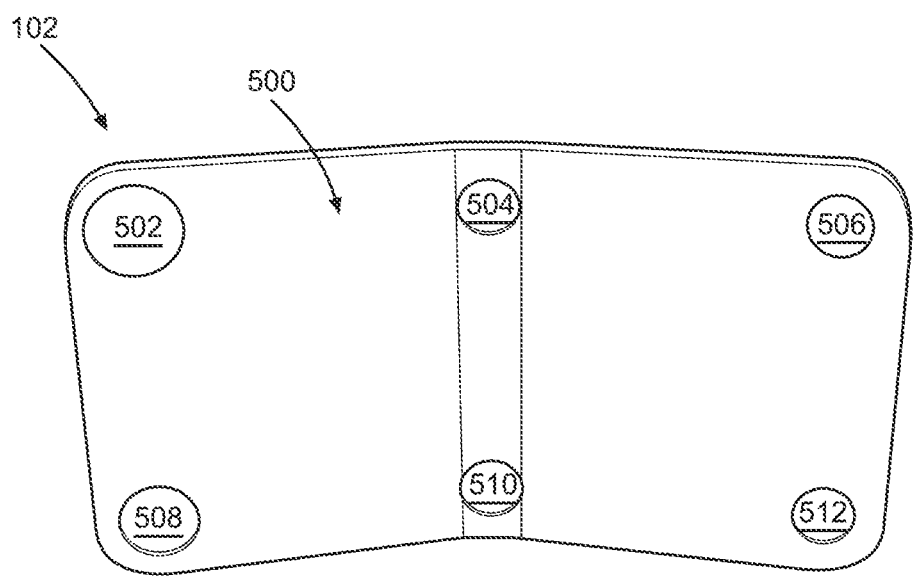
FIG. 5 is a diagram illustrating a type of perspective view of an exemplary embodiment.

A bottom surface 500 of the reference array platform 102 is shown in FIG. 5. For example, the reference array platform 102 may have a top surface with a reference array of two different codes as shown in FIG. 4A. The bottom surface 500 of the reference array platform 102 may be coated with an adhesive composition to promote adhesion of the bottom surface 500 to human skin or any other anatomical region. The bottom surface 500 may have one or more insertion areas 502, 504, 506, 508, 510, 512. In some embodiments, an insertion area 502, 504, 506, 508, 510, 512 may be a radio opaque insert. An insertion area 502, 504, 506, 508, 510, 512 may further have a depth of 0.5 mm. However, other embodiments may have an insertion area(s) with a different depth and size.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A physical instrument comprising:
a reference array platform, in a bent physical configuration, having a top surface and a bottom surface;
a reference array including at least two different fiducial markers, each in different respective code regions, disposed on the top surface of the reference array platform;
an intermediary panel of the top surface between a first code region of the top surface and a second code region of the top surface;
a first edge disposed on the top surface, the first edge shared by the intermediary panel and a first portion of a first fiducial marker in the first code region;
a second edge on the top surface, the second edge shared by intermediary panel and a first portion of a second fiducial marker in the second code region; and
an adhesive layer disposed on the bottom surface, the bent physical configuration based on a first fixed downward angle of at least a portion of the intermediary panel relative to one of the first and second code regions.

2. The physical instrument of claim 1, wherein the reference array comprises a plurality of distinct fiducial markers.

3. The physical instrument of claim 1, wherein each respective fiducial marker of the reference array is composed of a non-reflective material that absorbs light.

4. The physical instrument of claim 1, wherein the first code region comprises the first fiducial marker
wherein the second code region comprises the second fiducial marker.

5. The physical instrument of claim 4, wherein a third code region of the top surface of the reference array platform comprises a third fiducial marker in the reference array;
wherein the first code region is situated between the second and the third code regions; further comprising:
an additional intermediary panel of the top surface between the first code region of the top surface and the third code region of the top surface;
a third edge disposed on the top surface, the third edge shared by the additional intermediary panel and a second portion of the first fiducial marker in the first code region; and
a fourth edge on the top surface, the fourth edge shared by the additional intermediary panel and a first portion of the third fiducial marker in the third code region.

6. The physical instrument of claim 5, further comprising:
wherein the first, second and third fiducial markers each different from one another; and
wherein the bent physical configuration is further based on a second fixed downward angle of at least a portion of the intermediary panel relative to one of the first and third code regions.

7. A physical instrument comprising:
a reference array platform, in a tilted physical configuration, having a top surface and a bottom surface;
a reference array including one or more code regions disposed on the top surface of the reference array platform;
an intermediary panel of reference array between a first code region and a second code region; and
an adhesive layer disposed on the bottom surface, the tilted physical configuration based on a first fixed angle between a first edge of a first side portion of the reference array platform and a second edge of a second side portion of the reference array platform, the first side portion corresponds to the first code region on the top surface, the second side portion corresponds with the second code region on the top surface, the first code region comprising a first fiducial marker different than a second fiducial maker of the second code region;
wherein an intermediary edge of an intermediary side portion of the reference array corresponding to the intermediary panel, the intermediary edge situated between the first and the second edges.

8. The physical instrument of claim 7, wherein a third code region of the top surface of the reference array platform comprises a third fiducial marker in the reference array;
wherein the reference array platform comprises a third side portion that corresponds with the third code region;
wherein the first code region is situated between the second and the third code regions;
wherein a second fixed angle occurs between the first side portion and the third side portion.

9. The physical instrument of claim 8, wherein the first fixed angle is equal to the second fixed angle;
wherein both the first angle and second angle are one of: 170 degrees, 165 degrees and 160 degrees.

10. The physical instrument of claim 8, wherein the first fixed angle occurring between the first side portion and the second side portion comprises one of 160, 165 and 170 degrees.

11. The physical instrument of claim 1, wherein each respective fiducial marker in the reference array has a corresponding platform portion on the reference array platform, each fiducial marker's corresponding platform portion has a same square area size and a same thickness.

12. The physical instrument of claim 1, wherein the bottom surface further comprises at least one radio opaque insert.

* * * * *